United States Patent [19]

Dumitriu et al.

[11] Patent Number: 5,620,706
[45] Date of Patent: Apr. 15, 1997

[54] POLYIONIC INSOLUBLE HYDROGELS COMPRISING XANTHAN AND CHITOSAN

[75] Inventors: Severian Dumitriu; Esteban Chornet, both of Sherbrooke; Pierre Vidal, Rock Forest, all of Canada

[73] Assignee: Universite de Sherbrooke, Sherbrooke, Canada

[21] Appl. No.: 416,025

[22] Filed: Apr. 3, 1995

[51] Int. Cl.$^6$ .............................. A61K 9/10; A61K 9/14; A61K 47/36
[52] U.S. Cl. .................. 424/485; 424/486; 424/488; 424/499; 424/500; 424/501; 424/449; 252/315.3; 252/315.4; 514/944
[58] Field of Search ...................... 424/485–486, 424/499–500, 443, 445, 447, 448; 602/49, 52; 252/315.3, 315.4; 514/944

[56] References Cited

PUBLICATIONS

Aiba, S. (1989). *Int. J. Biol. Macromol.*, 11: 249–252.
Barnett, S. E. and S.J. Varley. (1987). *Ann. Roy. Coll. Surg. Eng.*, 69: 153–155.
Battilotti, M. and U. Barberini. (1988). *J. Molec. Catal.*, 43: 343–352.
Beldie, C., et al. (1989). *Biomaterials*, 10: 622–624.
Bogdansky, S. (1990). *Biodegradable Polymers as Drug Delivery Systems*, M. Chasin and R. Langer eds. Marcel Dekker, Inc., New York, pp. 231–259.
Brine, C.J. (1988) *Chitin and Chitosan*, G. Skjåk–Bræk, T. Anthonsen and P. Sandford, eds., London and New York: Elsevier Appl. Sci., pp. 679–691.
Burgos, H. (1986). *Eur. J. Clin. Invest.*, 16: 486–493.
Chavasit, V. and J.A. Torres. (1990). *Biotechnol Prog.*, 6: 2–6.
Chibata, I., et al. (1986) *J. Mol. Catal.*, 37: 1–24.
Crescenzi, V., et al. (1981). *ACS Symposium Series.*, 150: 331–347.
Daly, M.M. and D. Knorr. (1988). *Biotechnology Progress*, 4(2): 76–81.

Domszy, J.G., et al. (1986) *Chitin in Nature and Technology*, R. Muzzarelli, C. Jeuniaux and G.W. Gooday, eds., London and New York: Plenum Press., pp. 311–315.
Dumitriu, S., et al. (1994). *J. Bioactive Compat. Polym.*, 9: 184–209.
Dumitriu, S. et al. (1992). *Il Farmaco*, 47(4): 509–518.
Dumitriu, S., et al. (1990). *Clinical Materials*, 6: 265–276.
Fujuda, H. (1980). *Bull. Chem. Soc. Jpn.*, 53: 837–840.
Fujuda, H. and Y. Kikuchi. (1978). *Bull. Chem. Soc. Jpn.*, 51(4): 1142–1144.
Gianfreda, L. and M.R. Scarfi. (1991), *Molec. Cell. Biochem.*, 100: 97–128.
Goosen, M.F.A., et al. (1985). *Biotechn. Bioeng.*, 27: 146–150.

(List continued on next page.)

*Primary Examiner*—Edward J. Webman
*Attorney, Agent, or Firm*—Merchant, Gould, Smith, Edell, Welter & Schmidt, P.A.

[57] ABSTRACT

A method for the preparation of insoluble hydrogels from the complexation of polycations and xanthan is reported. Stable hydrogels capable of retaining between 65 and 95 % weight water were prepared particularly with chitosan and xanthan. The water retention and properties of the hydrogels were studied as a function of the degree of acetylation of chitosan and the ratio chitosan/xanthan used in the preparation of the gel. The chitosan-xanthan complex was used to immobilize biological material. Hydrogels containing enzymes (for example endo-1,4-β-xylanase and protease) either as single enzymes or as a binary system have been prepared. Immobilization varied between 85 and 98 %. The immobilized xylanase activity was significantly greater with respect to the free enzyme while the binary enzyme system promoted protease activity. Other hydrogels prepared with polybasic drugs complexed to xanthan with or without chitosan have been prepared. These complexes slowly dissociate in acidic media and provide for sustained release of compounds in near neutral pHs. Gels containing chitosan are stable in all physiological pHs and the immobilized molecules are released therefrom by diffusion.

4 Claims, 3 Drawing Sheets

OTHER PUBLICATIONS

Grywnowicz, K., et al. (1993). *J. Molec. Cat.*, 80: 117–125.
Guit, R.P.M. et al. (1991). *Biotechn. Bioeng.*, 38: 727–732.
Hirano, S. et al. (1990). *Proceedings of the ACS Division of Polymeric Materials Science and Engineering*, 62: 492–496.
Hirano, S. and K. Horiuchi. (1989). *Int. J. Biol. Macromol.*, 11: 254–255.
Hirano, S., et al. (1978). *Biopolymers*, 17: 805–810.
Hisamatsu, M. and T. Yamada. (1989). *J. Ferment. Bioeng.*, 67(3): 219–220.
Jamuna, R. S.V. Ramakrishna. (1992). *Enzyme Microb. Technol.*, 14: 36–41.
Kennedy, J.F. and M. Paterson. (1993). *Polymer International*, 32: 71–81.
Kifune, K. (1992). *Advances in Chitin and Chitosan*, C.J. Brine, P.A. Sandford and J.P. Zikakis, eds., Elsevier Appl. Sci. pp. 9–15.
Kikuchi, Y. and N. Kubota. (1985). *Makromol. Chem., Rapid Commun.*, 6: 387–390.
Kikuchi, Y. and N. Kubota. (1985). *J. Polym. Sci., Polym. Lett. Ed.*, 23: 537–543.
Kikuchi, Y. and A. Noda. (1976). *J. Appl. Polym. Sci.*, 20: 2561–2563.
Kikuchi, Y. and H. Fukuda. (1974). *Makromol. Chem.*, 175: 3593–3596.
Kim, K.-S. and C.K. Rha. (1989). *Chitin and Chitosan*, G. Skjåk-Bræk, T. Anthonsen and P. Sandford, eds., London and New York: Elsevier Appl. Sci., pp. 617–625.
Kise, H. and A. Hayakawa. (1991). *Enzyme Microb. Technol.*, 13: 584–588.
Kise, H., et al. (1987). *Biotechnol. Lett.*, 9(8): 543–548.
Lemainque, A., et al. (1988). *Eur. J. Biochem.*, 174: 171–176.
Mansfeld, M. et al. (1991). *Enzyme Microb. Technol.*, 13: 240–244.
Melia, C.D. (1991). *Critical Rev. Therap. Drug Carrier Systems*, 8(4): 395–421.
Mireles, C., et al. (1992). *Advances in Chitin and Chitosan*, (C.J. Brine, P.A. Sanford, J. P. Zikakis, Eds.), Elsevier Appl. Sci., pp. 506–515.
Mitsutomi, M., et al. (1985). *J. Ferment. Technol.*, 63(4): 325–329.
Nilsson, K., et al. (1983). *Nature*, 302: 629–630.
Peleg, K. and C. Rha, (1988). *J. Rheol.*, 32(4): 367–385.
Peppas, N.A. and A.G. Mikos. (1986) *Hydrogels in Medicine and Pharmacy, vol. 1, Fundamentals*, N.A. Peppas, ed., Boca Raton, FL: CRC Press. Inc., pp. 2–25.
Phadke, R.S. (1992). *BioSystems*, 27: 203–206.
Puls, J., et al. (1988). *Methods in Enzymology*, vol. 160, V.A. Wood and S.T. Kellogg, eds., New York: Academic Press, Inc., pp. 528–536.
Rathke, T.D. and S.M. Hudson. (1994). *J.M.S.–Rev. Macrobiol. Chem. Phys.*, C34(3): 375–437.
Roberts, G.A.F. and J.G. Domszy. (1982). *Int. J. Biol. Macromol.*, 4: 374–377.
Scheirer, W., et al. (1984) *Develop. Biol. Standard.*, 55: 155–161.
Shaw, J.-F., et al. (1990). *Biotechnol. Bioeng.*, 35: 132–137.
Shioya, T. and C.K. Rha (1989). *Chitin and Chitosan*, G. Skjåk-Bræk, T. Anthonsen and P. Sandford, eds., London and New York: Elsevier Appl. Sci., pp. 627–634.
Simionescu, C. et al. (1986). *Reactive Polymers*, 4:237–241.
Simpson, H. D., et al. (1991). *Biochem. J.*, 277 (Pt. 2): 413–417.
Struszczyk, H. (1987). *J. Appl. Polym. Sci.*, 33: 177–189.
Uo, M., et al. (1992). *J. Ceramic Soc. Jpn.*, 100(4): 430–433.
Yoshioka, T., et al. (1990) *Biotechnol. Bioeng.*, 35: 66–72.
Zielinski, B.A. and P. Aebischer. (1994). *Biomaterials*, 15(13): 1049–1055.

POLYIONIC INSOLUBLE HYDROGELS COMPRISING XANTHAN AND CHITOSAN

FIELD OF THE INVENTION

This invention relates to hydrogels made of polyionic complexed molecules, particularly to hydrogels for use in slow release formulations of biologically active molecules.

BACKGROUND OF THE INVENTION

Hydrogels can be classified into two broad categories: reversible and irreversible. The former are characterized by significant changes in the rheological properties as a function of temperature, ionic concentration, and dilution. Irreversible hydrogels are soluble in water, as well as in other solvents, over a wide range of temperatures and dilutions. Due to their solubility profiles, irreversible hydrogels have multiple applications in food, cosmetics, medicine and biotechnology [1–5]. The preparation of hydrogels can be achieved by a variety of methods: reticulation of linear polymers; grafting of synthetic polymers onto naturally occurring macromolecules; chelation of polycations; and complexation between polyanions and polycations [6–8].

Chitosan, the deacetylated form of chitin (N-acetyl glucosamide), has polycationic properties and forms, with polyanions, water insoluble hydrogels [9–14]. These have been successfully used as a support material for the immobilization of enzymes and cells [15–20] and for controlled drug release [20–24]. The immobilization of enzymes using organic and inorganic matrices has been widely studied [12,25–29] and a variety of immobilization methods such as chemical reaction, microencapsulation, and adsorption on various surfaces have been used [30–33]. Our attention has focused on enzyme immobilization using hydrogels because their hydrophilicity allows, in principle, for the creation of microsystems favourable for enzymatic activity. Complexes of cationic polymers have been prepared with different polyanions like synthetic polyanions (polyacrylic, polymethacrylic acids and polyvinyl alcohol sulfate [49–51]; natural polyanions (alginate, heparin, carrageenan, pectin, glycosaminoglycanes. [52–54]; cellulosic derivatives (carboxymethylcellulose and oxidized cellulose [58–59]). Complexes of natural polyions such as chitosan, carboxymethylcellulose and alginic acid are already known [8,34,36], and enzymes and other bioactive compounds have been immobilized or lodged therein [37–38]. All the hydrogels known in the art have however a capacity of encapsulation of biological products (medication, enzymes and cells) which retention yield is very low, varying from 1 to 8%. In all these cases, the enzymes conserve only 50% of their initial activity. Therefore, there is clearly a need for polyionic hydrogels showing a more performing retention yield as well as an improved activity for the retained enzymes.

SUMMARY OF THE INVENTION

It is an object of the present invention to provide hydrogels having high retention yields of biological products. Not only do the hydrogels of this invention have a very good retention yield, they also preserve and/or enhance the activity of complex molecules like proteins and enzymes immobilized therein. These hydrogels comprise a polycationic molecule like chitosan or polybasic drugs as a natural polycation complexed with xanthan as a polyanion.

In a preferred embodiment, the polycationic molecule is chitosan. Hydrogel composition depends on the acetylation degree of the chitosan which will determine the charges of this compound and its ability to complex to xanthan. The swelling capacity of the hydrogels depends on the molecular weight of the chitosan component, its acetylation degree and also on the surface area of the prepared products, being microspheres, spheres and films/sponges.

In a preferred embodiment of the present invention, the biological products encapsulated and immobilized in chitosan/xanthan hydrogels are enzymes. For all enzymes tested, as single or combined enzymes, the retention yield varies from 80 to 98%. The enzymes are included in proportions that are up to 25% of the hydrogel mass. These enzymes are slowly released by diffusion from the hydrogels. When compared to the activity of the free enzymes, the activity of encapsulated enzymes may be improved by 2 Or 3 fold.

In another embodiment of the invention, a large panel of neutral drugs have been encapsulated in chitosan/xanthan hydrogels. These neutral drugs have been shown to be released from the gels following zero order kinetics.

In another embodiment of the invention, polybasic drugs have been complexed with xanthan with or without chitosan. This system releases the drug at neutral and acidic pHs also following a zero order kinetics.

The advantages of the hydrogels of the present invention are conferred by the preservation of the biological activities of the immobilized molecules. Also, the hydrogels containing chitosan are stable in acidic pHs, a characteristic very useful for per os administration of medications. The hydrogels will disintegrate only in basic solutions which pH is equivalent to the pH of a 10% NaOH solution. The hydrogels are therefore stable in all encountered physiological pHs. When polybasic drugs are directly complexed with xanthan, the former are slowly dissociated from the latter in acidic conditions and the speed of dissociation decreases as the pH increases. A sustained release is achieved at pH of 6 to about 8, which makes the compositions useful for external use (applied to the skin pH 6.5) as well as for internal use.

DESCRIPTION OF THE INVENTION

Hydrogels made of polycationic and polyanionic compounds have been the subject of many studies. A study conducted by Kim and Rha [36] has shown that hydrogels might be good substrates for immobilized cells. The results obtained with regard to improved cell adhesion and growth cannot however be applied to predict the improvement of immobilization and activity of molecules like enzymes. The conformation of enzymes is rarely predictable and the enzymes are most often very capricious towards environmental conditions that will determine their conformation and their degree of activity. Therefore, even though the encapsulation of cells has been made with success, encapsulation of enzymes has not shown a great improvement with regard to the retention of enzymes in hydrogels and most importantly, the preservation of the biological activity of such encapsulated enzymes.

The use of natural polyanionic substances in the formation of complexes with polycations is already known. Indeed, alginates, heparin, carrageenan, pectin, glycosaminoglycans already been tried. However, the retention capacity of complex molecules like enzymes in these hydrogels is far from excellent (between 1 and 8%). Moreover, the enzymes immobilized in these hydrogels loose about 50% of their activity. Xanthan is a known polyanion. Although this polysaccharide produced by *Xanthomonas campestris* might be on first sight another natural polyanion among others, its complexation with a polycation like chitosan revealed, in accordance with the present invention surprisingly good properties with regard to the retention yield of enzymes and the preservation or enhancement of the activity of such immobilized enzymes.

In the present invention, other polycations might be used in lieu of chitosan. For example, a complex made of xanthan and polybasic drugs has provided good insoluble hydrogels having high retention capacities and showing stability in acidic media.

A full description of this invention is made hereinbelow by way of examples and figures which purpose is to illustrate the invention rather than to limit its scope.

MATERIALS AND METHODS

Figure 1:
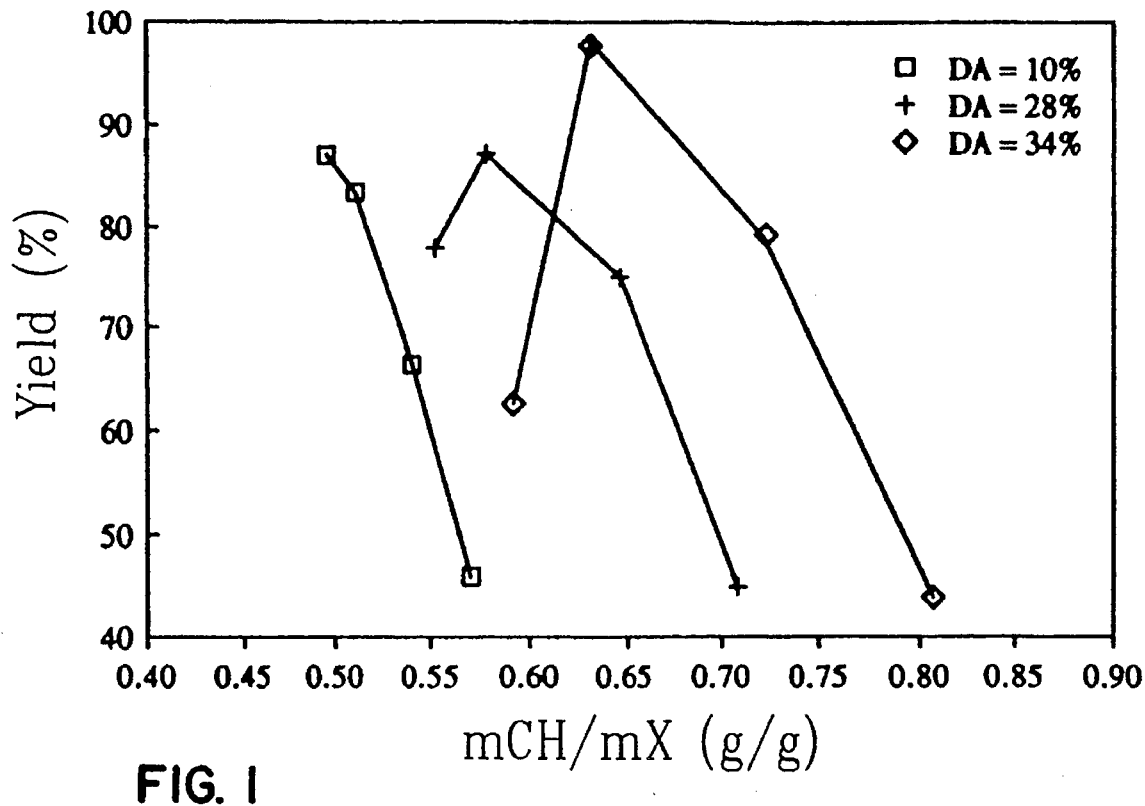
FIG. 1 shows the complexation yield of chitosan as a function of the chitosan/xanthan ratio for three samples of chitosan having different acetylation degrees (10, 28 and 34%). pH of the solution: 6.3.

Xanthan (X) (Aldrich, batch no. 08403HY) was purified by dissolution in water (1 wt % of xanthan) and precipitation with isopropyl alcohol. Four dissolution-precipitation cycles were used to lower the N content from 0.7 wt % (initial xanthan) to 0.15 wt % in the purified xanthan. The latter was dissolved again in water (1 wt %), precipitated with ethyl alcohol (50/50 v/v), filtered and rinsed with ethyl alcohol/water mixtures (varying from 2/1 to 1/2 by volume). The resultant xanthan was again dissolved in water (1.5 wt %) and lyophilized. The N content was 0.09 wt %. Solutions of this xanthan were prepared by adding 3.5, 5.45 and 6.5 g to 1000 mL of water for preparing microspheres, spheres and films, respectively.

Chitosan (CH) were dissolved in 300 mL of 0.1 N HCl. The solution neutralized with 0.1 N NaOH, and distilled water was added for a total volume of 1000 mL at pH=6.3. Two chitosan samples with degrees of acetylation (DA) of 28% and 10% were derived from the Sigma chitosan (DA= 34%; batch no. C-0792) using alkaline hydrolysis (30% NaOH) at room temperature for 1 h and 2.5 h, respectively.

EXAMPLE 1

The hydrogel was prepared by mixing 61.5 mL of the chitosan solution with 61.6 mL of the xanthan solution. Agitation was conducted for 10 min at room temperature and the hydrogel formed was separated out by centrifugation at 3000 rpm. The hydrogel was washed repeatedly with water to remove the free chitosan and xanthan which were monitored for in the wash water by HPLC (xanthan and chitosan) and by titration of the amine groups on chitosan.

EXAMPLE 2

The chitosan (CH/X) hydrogels were also prepared as spheres in the following way: 30 mL of the chitosan solution were added dropwise, with a syringe, into 20 mL of the xanthan solution previously degassed. Spheres formed under mild agitation at room temperature. The spheres were collected and washed with an acetate buffer solution (0.2 M, pH=3.6) to eliminate the excess free chitosan. The spheres were then rinsed with water. The spheres were kept in an acetate buffer, 0.25M, at pH=3.6.

EXAMPLE 3

Solutions of chitosan (having different degrees of acetylation (10, 28 and 34%) were prepared as follows: 6.5 g chitosan were dissolved in 1% acetic acid and precipitated with 10% NaOH. The precipitated chitosan was successively washed with water (4–5 L), alcohol/water (50/50 v/v) alcohol (95%). The purified chitosan was then dried by lyophilization. Different solutions of chitosan were made as follows:

For microspheres, 3.5 g chitosan were dissolved in 100 mL HCl 1N, neutralized with NaOH 1N till a pH=3.8 is obtained, and then the volume of the solution was made one liter with water. The electrolyte concentration was 0.09M NaCl;

For spheres (1–2 mm), 5.45 g chitosan were dissolved in 300 mL HCl 1N, neutralizes with NaOH 1N till a pH=5.5 was obtained, and the volume of the solution completed to one liter with water. The electrolyte concentration 0.18M NaCl;

For films, 6.5.g chitosan were dissolved in 300 mL HCl 1N, neutralized with NaOH 1N till a pH=6.5 was obtained. After volume completion to one liter with water, the electrolyte concentration was 1.8M NaCl.

Solutions of chitosan and xylan are degased.

For preparing the microspheres, to 20 mL of a 0.35% xanthan solution placed in a reactor with an agitating system is added 20 mL of a 0.35% chitosan solution with the aid of a syringe of a diameter of 0.1 mm. The diameter of the microspheres depend on the speed of agitation, the syringe diameter and the speed of introduction of chitosan in the xanthan solution. We have tested a speed of agitation of 500 rev./min. and a speed of introduction of chitosan 0.5–2 mL/min. After the addition of chitosan is completed, the mixture is kept under agitation for 30 minutes. The reaction mixture is then diluted with 200 mL acetate buffer 0.1M pH=5.6. The microspheres are decanted and washed with 500 mL of the same buffer until no free xanthan or chitosan is left (verified by isopropyl alcohol precipitation for xanthan and by NaOH 10N precipitation for chitosan). The microspheres are kept in the same buffer for further use.

For preparing the spheres, a 20 mL chitosan solution (0.545%) is introduced in a reacher, and a 20 mL xanthan solution of varying concentration is added at a speed of introduction of 0.5 mL/min with the aid of a 0.2–0.5 mm diameter syringe under low speed of agitation to avoid aggregation of the spheres. The preparation is further processed like for the microspheres. The spheres have a diameter varying from 1.5 to 2 mm diameter.

For preparing films, 12 mL of a xanthan solution (0.65%) was poured into a 100 mm Petri plate. On a perfectly plane surface, the solution was allowed to rest for at one hour to obtain a layer of homogenous thickness. 20 mL of a chitosan solution was added with a syringe, taking care for not disturbing the xanthan layer. These two phases are allowed to stay for two hours. The formed film is taken from the plate walls. The reaction further proceeds at room temperature for at least four days. The solution formed at the top of the film is withdrawn with a syringe, and the film is washed in the following successive solutions;

10 mL acetate buffer 0.1M, pH 5.3 (3×30 minutes);

10 mL CaCl$_2$ 1% (2×30 minutes); and 10 mL NaCl 2% (4×30 minutes); and 25 mL water (5×30 minutes ).

Sponges can be also made following substantially the same procedure as for preparing films, but changing the drying procedures for enhancing the size of the pores formed in the films.

The react ion yields were determined using the following relationship:

$$\text{yield} = \frac{\text{(weight of dry gel)}}{\text{(weight of chitosan)} + \text{(weight of xanthan)}} \times 100 \quad \text{EQUATION 1}$$

The degree of swelling, $\alpha$, of the hydrogels was determined by weighing the dry hydrogels before and after immersion in the acetate buffer at 2 min intervals, and was defined as:

$$\alpha = \frac{\text{(weight of hydrated gel)} - \text{(weight of dry gel)}}{\text{(weight of dry gel)}} \times 100 \quad \text{EQUATION 2}$$

By plotting $\alpha$ versus time of immersion the saturation value was determined when $\alpha$ reaches a plateau, which corresponded to $\alpha_{max}$. From this plot, the swelling capacity, Q, was determined:

$$Q = \frac{\text{[weight of gel at maximum swelling]}}{\text{[weight of dry gel]}} \quad \text{EQUATION 3}$$

The water content, W, of the hydrogel at equilibrium was determined by:

$$W = \frac{\text{(weight of gel at maximum swelling)} - \text{(weight of dry gel)}}{\text{(weight of gel at maximum swelling)}} \times 100$$

The degree of acetylation, DA, of chitosan was determined from elemental N analysis date using the following relationship:

$$DA = \left[ \frac{(8.695 - \%N)}{1.799} \right] \times 100 \quad \text{EQUATION 5}$$

where 8.695 is the % N of a completely deacetylated chitosan, and 1.799 is the difference between 8.495 and 6.896. This latter value is the N % in completely acetylated chitin.

The FTIR spectra were carried out using a Nicolet (model 5DXB) spectrometer operated in the 400–4600 cm$^{-1}$ region, and 400 scans were collected at a resolution of 4 cm$^{-1}$. The samples were prepared by mixing KBr with either chitosan, xanthan or the polygel. Typically, 3.5 mg of organic material were mixed with 350 mg of KBr. The mixture was well blended and finely ground for 1 m in after which a pellet was prepared at a pressure of 1.0 MPa. The pellet was dried under vacuum, at room temperature, for a period of 24 h in the presence of P$_2$O$_5$.

The hydrogel samples to be used for the transmission and scanning electron microscopic observations (TEM, SEM) were stabilized with glutaraldehyde (1 wt %) in a 0.1M phosphate buffer at pH=7.2 for 15 to 60 min at 4° C. Then these samples were washed repeatedly with a 0.1M phosphate buffer solution. The samples were then post-fixed in 1% osmium tetroxide (OsO$_4$) in a 0.1M phosphate buffer at pH=7.2 for 24 h at 4° C. After repeated washings with the buffer solution, the samples were dehydrated sequentially with ethanol solutions with increasing ethanol concentration (30, 50, 70, 90, 95, 100 vol %).

For SEM the ethanol impregnated gel samples were totally dried by the critical point drying method (CPD) using CO$_2$. The dried samples were then fixed on aluminium sample holders using a silver based adhesive. The samples were made conductive by sputter coating (Anatech Ltd., model Hummer VI) with a 15 nm layer of Au/Pd. A JEOL JSM-840A scanning electron microscope operated under an accelerated voltage of 15 or 20 kV was used for the observations.

For TEM, the samples were dehydrated with 100% ethanol, placed into liquid propylene oxide for a few minutes and then into a 1:1 mixture of propylene oxide and epoxy resin (EPON) overnight. After that, the samples were transferred into pure epoxy resin and placed in an oven at 60° C. for 48 h to polymerize. After polymerization, ultra-thin sections, 600 Å in thickness, were made and stained with uranyl acetate and lead citrate. The thin sections were examined under a Philips EM 300 transmission electron microscope at an accelerating voltage of 60 kV.

The immobilization of the enzymes was carried out as follows: to an aqueous solution of xanthan (0.65 wt %), the enzymes [endo-1,4-β-xylanase from Trichoderma viride, 2.5 U/mg (Fluka); protease type XIX fungal from *Aspergillus sojae*, 0.4 U/mg (Sigma); or enzyme mixtures at various ratios] were added at concentrations varying between 0.5 and 1.8 wt %. The solution was agitated for 15 min at 15° C. and introduced dropwise, with a syringe, into the chitosan solution. The latter was adjusted to pH=6.3 for the protease preparations and to pH=4.3 for the xylanase preparations alone. The microspheres formed were agitated for 15 minutes at room temperature (20°–29°C.) and washed with an acetate buffer (0.5M, pH=5.3). They were then kept at 5° C. in an acetate buffer (0.05M, pH=5.3).

The enzymatic activity of the immobilized xylanase and protease was determined using the following established methods [39–40].

Protease Assay

A 2% hemoglobin solution was prepared by dissolving (with gentle stirring) 5 g of hemoglobin substrate powder (SIGMA) in a solution of 80 g of urea in 80 mL of water. After incubation at 37° C. for 60 min, 50 mL of 0.25M buffer were added. The pH was adjusted to 7.2 and then the solution was diluted to 250 mL with water. When casein or other protein was used, the substrate solution could be prepared without urea. All the solutions were equilibrated at 25° C. before use. The assay was started by adding 5 mL of temperature-equilibrated substrate solution to 0.02 g of immobilized protease and mixed thoroughly but gently to prevent frothing. The mixture was incubated at the desired temperature for a fixed period of time not exceeding 10 min. Multiple assays were performed by adding substrate to successive tubes in 30 sec intervals. The reactions were terminated in the same sequence. At the end of the incubation period, the reaction was terminated by adding 10 mL of 5% trichloroacetic acid to the assay mixture. A blank was prepared by combining the trichloroacetic acid with the immobilized enzyme and then substrate was added. The assay mixture and blank were allowed to stand for 30 min. The precipitate material was removed by centrifugation. The absorbance of the supernatant was measured at 280 nm, with reference to the blank. One unit of enzyme activity is defined as the amount of enzyme required to cause a unit increase in absorbance at 280 nm across a 1 cm path length, under the conditions of the assay. The enzymatic activity was expressed in activity units per unit weight of the dry microsphere.

Xylanase Assay

A Remazol Brilliant Blue R-Xylan (RBB-xylan) solution in 0.05M acetate buffer, pH 5.4, 5.75 mg/mL was used. Immobilized enzyme (0.02 g) was mixed with 0.5 mL of preheated (30° C.) RBB-xylan (5.75 mg/mL) solution and incubated at 30° C. The reaction was terminated by the addition of 1. mL of ethanol to precipitate the unhydrolyzed RBB-xylan and the high molecular weight fragments. After standing for 30 min at room temperature (thermal equilibration of samples), the precipitated substrate was recovered by centrifugation at 2000 g for 1.5 min. The absorbance of supernatant was measured at 595 nm against the respective substrate blank. The enzymatic activity was expressed in activity units per unit weight of the dry microsphere. The effective diffusion coefficient of RBB-xylan in the hydrogel was calculated from the changes in the solution concentration determined by absorption at 595 nm.

Other assays using cells, drugs and enzymes:

The behavior of other immobilized and co-immobilized enzymes (lipase and hemicellulase with or without xylanase) has also been verified. Furthermore, chitosan/xanthan hydrogels incorporating neutral drugs have been made. Typical neutral drugs include cephalosporin, tetracycline, oxytetracycline, sulfathiazole, metronidazole, chloramphenicol, daunorubicin, ampicillin, penicillin, erythromycin, quinidine, alacacinomycin and mithramycin. The same hydrogels may also be used as a support for eucaryotic and procaryotic cells. Gels can also be made by substituting a part or the totality of the chitosan by other polycations. Examples of polycations are polybasic drugs like gentamycin, bleomycin, anthelmycin, enzomycin A, vancomycin, trichomycin, adenomycin, orthomycin, neomycin, kanamycin and sisomycin.

RESULTS AND DISCUSSION

The complexation reaction between the polyions leads to structural changes in both xanthan and chitosan polymers. A water insoluble hydrogel was formed by blocking the hydrophillic functions (R-COOH in case of polyanions and R'—$NH_2$ for the polycations) and by the interaction between the macromolecular chains. The latter effect created an "ionic" reticular network that immobilized the polymers. The hydrogel formed incorporated a significant amount of water and was capable of stabilizing biological products in the matrix.

Figure 2:
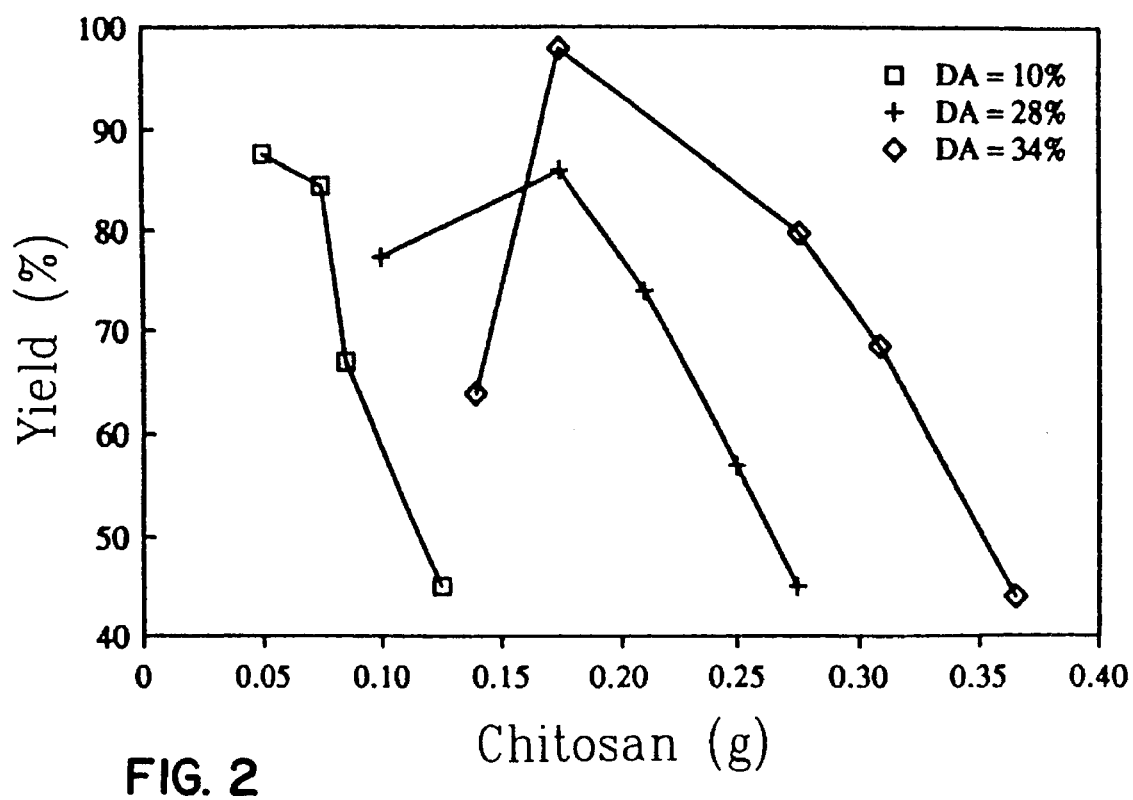
FIG. 2 shows the complexation yield of chitosan as a function of the quantity of chitosan in a 123 mL solution with 0.4 g xanthan. pH of the solution: 6.3.

We studied the complexation reaction between xanthan and chitosan by determining the yields and the structure of the complexes formed as well as the swelling. capacities. Three chitosan samples with degrees of acetylation (DA) of 10, 28 and 34% Were used. FIGS. 1 and 2 show the efficiency (yield) of the complexation reaction as a function of the xanthan/chitosan ratio and the mass concentration of chitosan, respectively. The complexation efficiency was as high as 90% of the available chitosan. The less deacetylated chitosan (DA=34%) formed a stable hydrogel with the highest chitosan/xanthan ratio. In fact, the lower the DA the greater amounts of xanthan were needed to form a stable hydrogel.

For the same degree of acetylation (DA=10%), the yield of formation of spheres, microspheres and films depends on the chitosan/xanthan ratio, as shown in Table 1.

TABLE 1

Variation in the complexation yield as a function of the CH/X ratio for various forms of hydrogels

| Ratio CH/X | Yield of complexation (%) | | |
|---|---|---|---|
| (g/g) | Microspheres | Spheres | Films |
| 0.2 | 89 | 90 | 98 |
| 0.5 | 98 | 87 | 93 |
| 0.7 | 85 | 83 | 90 |
| 0.9 | 76 | 81 | 73 |
| 1.2 | 58 | 69 | 53 |

The chitosan content of the hydrogel (spheres) was determined from the N content which depended upon the degree of chitosan acetylation and, to a lesser extent, on the CH/X ratio used in the complexation reaction, as shown in Table 2.

TABLE 2

Composition of the hydrogels as a function of the degree of acetylation

| Sample | Ratio CH/X[a] (g/g) | N Content of Hydrogel (%) | Composition Chitosan (%) | Xanthan (%) |
|---|---|---|---|---|
| 1 | 0.492 | 3.30 | 38.8 | 61.2 |
| 2 | 0.507 | 3.38 | 39.7 | 60.3 |
| 3 | 0.540 | 3.41 | 40.1 | 59.9 |
| 4 | 0.570 | 3.52 | 41.4 | 58.6 |
| 5 | 0.555 | 2.04 | 24.9 | 75.1 |
| 6 | 0.580 | 2.28 | 27.8 | 72.2 |
| 7 | 0.642 | 2.31 | 28.2 | 71.8 |
| 8 | 0.707 | 2.40 | 29.3 | 70.7 |
| 9 | 0.592 | 1.96 | 24.3 | 75.7 |
| 10 | 0.628 | 2.10 | 26.0 | 74.0 |
| 11 | 0.720 | 2.25 | 27.8 | 72.2 |
| 12 | 0.807 | 2.38 | 29.5 | 70.5 |

| Sample | % N in Chitosan | DA (%)[b] |
|---|---|---|
| 1–4 | 8.51 | 10 |
| 5–8 | 8.19 | 28 |
| 9–12 | 8.08 | 34 |

[a]CH/X = chitosan to xanthan.
[b]DA = degree of acetylation.

The results indicate that a higher DA lowered the chitosan content of the complex due to a decrease in the, free amine available for complexation. The chitosan content in the hydrogel increased with the CH/X ratio in the reaction.

The method of preparation of the hydrogels (microspheres, spheres and films) was determinant in their composition, as shown in Table 3.

TABLE 3

| Hydrogel Types | Composition (%) | |
|---|---|---|
| | Chitosan | Xanthan |
| Microspheres | 46.1 | 53.9 |
| Spheres | 39.7 | 60.3 |
| Films | 26.8 | 73.2 |

Initial CH/X = 0.5 g/g; DA chitosan = 10%; Mn chitosan = 691,390. The pH value is specific to each type of preparation (See Materiala and Methods)

We studied the influence of the pH of the chitosan solution on the yield of complexation with xanthan. The results are shown in Table 4.

TABLE 4

Influence of the pH of the chitosan solution (0.65 wt %) on the complexation with xanthan

| pH | Xanthan Complexation (%) |
|---|---|
| 1.5 | 21 |
| 2.5 | 36 |
| 3.5 | 56 |
| 4.5 | 60 |
| 5.5 | 78 |
| 6.3 | 98 |

Chitosan to xanthan ratio (CH/X) = 0.65 g/g.
M chitosan = 691,390 determined by measuring the intrinsic viscosity.
$[\eta] = 1.81 \times 10^{-3} \, M^{0.93}$; the value 0.93 being determined in 0.1 M acetic acid/0.2 M NaCl solution at 25° C. [35].

Poor complexation at low pHs was observed due to strong protonation of the amine groups which impeded the reaction with the carboxylic groups present in the xanthan. Similar results have been reported for the complexation of chitosan with CMC and alginic acid [8,36].

The molecular weight of chitosan had a strong influence on the properties of the hydrogel, particularly the water retention capacity and the solubility under basic conditions. The effect of molecular weight on water retention was studied using four samples of chitosan with similar degrees of acetylation but molecular weights varying from 691,930 to 122,350. The results are shown in Table 5.

TABLE 5

Influence of the molecular weight of chitosan on the absorption of water by the chitosan-xanthan hydrogel

| Chitosan[a] $M_a$ | DA[b] of Chitosan (%) | Complexation yield (%) | $\alpha_{max}$[c] (%) |
|---|---|---|---|
| 691,930 | 28.0 | 98.9 | 560 |
| 452,875 | 27.9 | 97.2 | 805 |
| 191,325 | 28.2 | 84.5 | 992 |
| 122,350 | 28.8 | 81.3 | 1050 |

[a]Determined by measuring the intrinsic viscosity $[\eta] = 1.81 \times 10^{-3} \, M^{0.93}$ in 0.1 M acetic acid/0.2 M NaCl solution at 25° C. [35].
[b]DA = degree of acetylation.
[c]$\alpha_{max}$ = maximum hydrogel swelling.
pH = 5.0: buffer acetate 0.2 M.

The decomposition of the chitosan-xanthan hydrogel in basic media depended on the pH and the ionic concentration of the buffer solution. In the pH range between 7.0 and 9.2, the hydrogel is stable and independent of the ionic concentration. At pH>9.2, decomposition of the complex begins at 2M Concentration. In a 10 wt % NaOH solution the complex broke down completely.

The FTIR spectra of the hydrogels have the characteristic absorption bands of chitosan and xanthan (data not shown). The chitosan spectrum has the following characteristic absorption bands: the amide I band (C=O stretching vibration at 1653 $cm^{-1}$)and amide II band (N—H bending and C—N stretching). The spectrum shows that the material has a low degree of acetylation at 1599 $cm^{-1}$ and shoulder at 1563 $cm^{-1}$. The characteristic bands for xanthan are due to C=O stretching of the ester groups at 1730 $cm^{-1}$ and of the H-bonded or ionized carboxylic groups at 1650 $cm^{-1}$ and lower frequencies. Complexation did not affect the behavior of the ester group which showed as expected a less intense absorption around 1730 $cm^{-1}$. All the other C=O absorptions from carboxylic groups mentioned shove collapse after complexation to form a single large band centered at 1620 $cm^{-1}$. The amide II is seen as a shoulder. We noted that the 1620 $cm^{-1}$ band in the chitosan-xanthan gel is stronger than that of xanthan due to the conjugation between the $COO^{-1}$ and $NH_3^+$ groups.

Figure 3A:
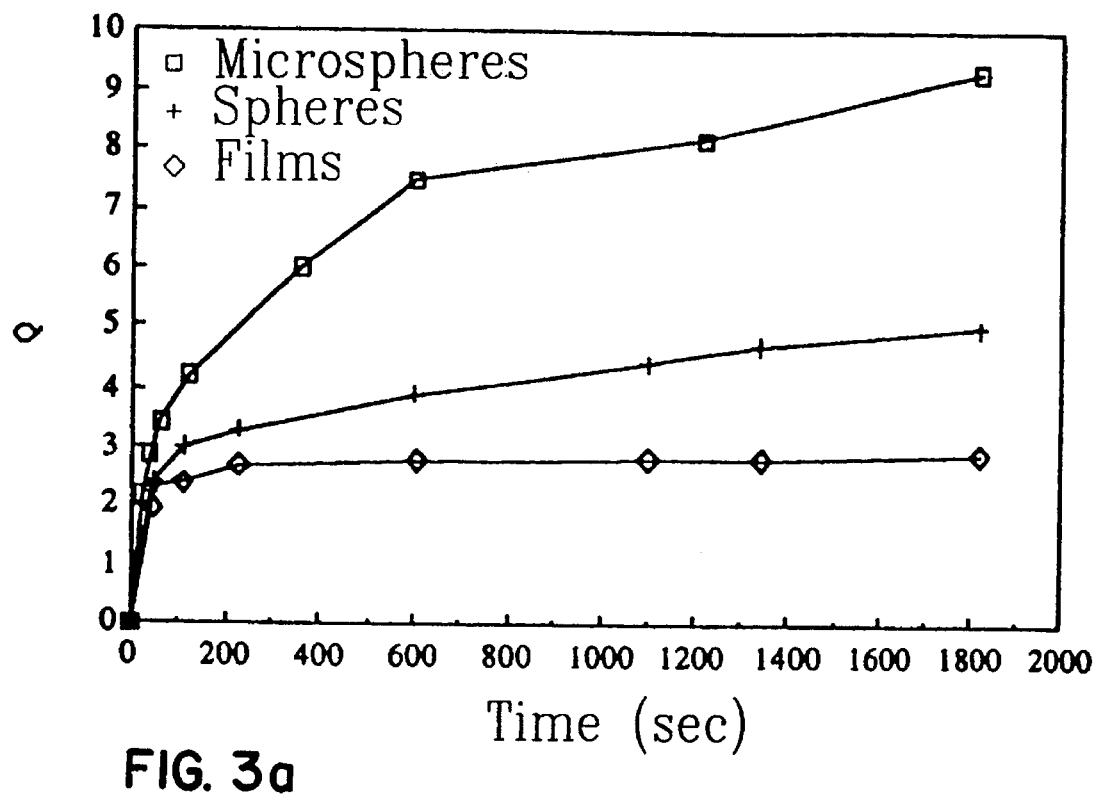
FIGS. 3a, b and c show the swelling capacity (Q) as a function of time at different pHs: 3.6, 5.0 and 8.0. The chitosan has an acetylation degree of 10%.
Figure 3B:
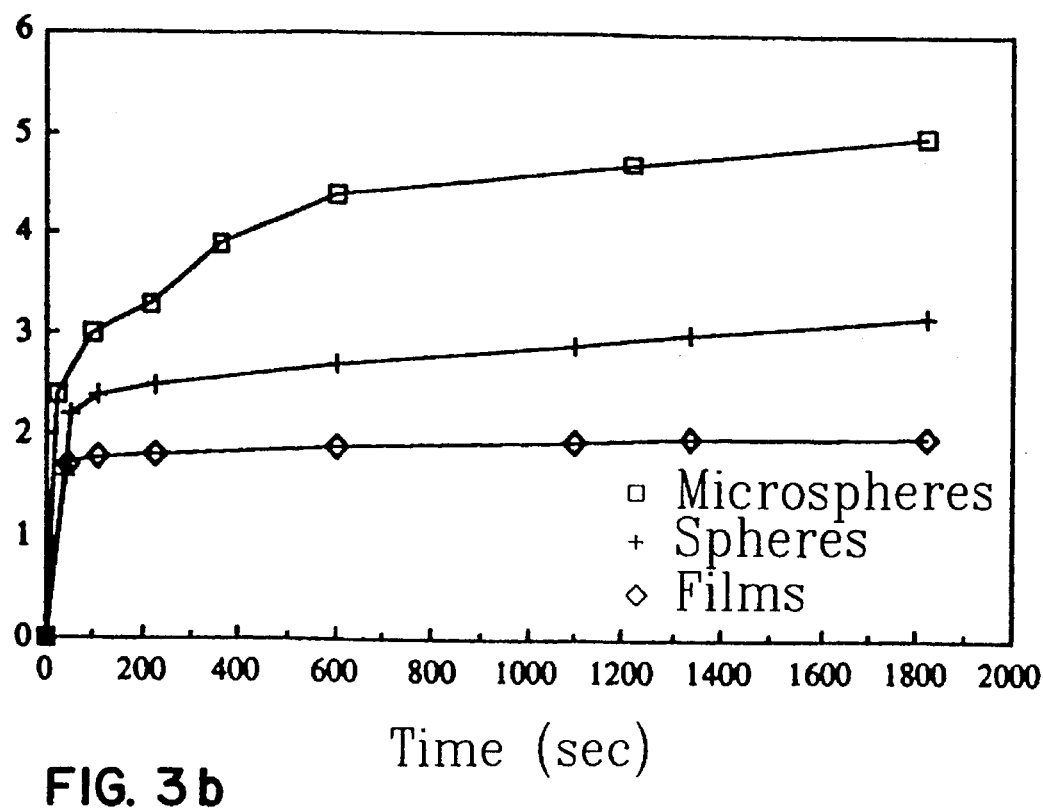
Figure 3C:
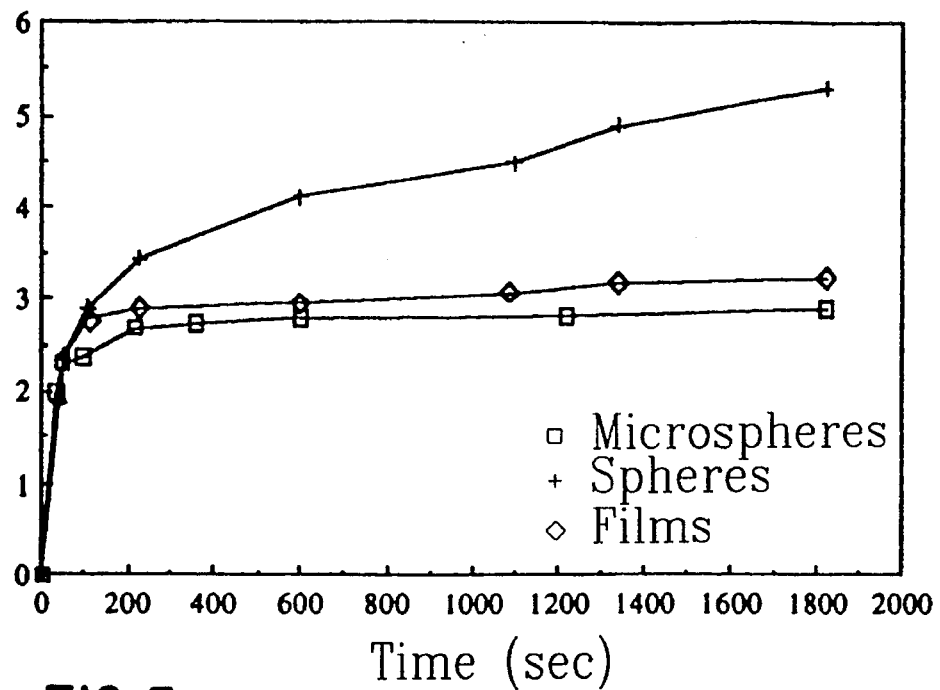

The swelling properties of the hydrogels were studied in buffer solutions (0.2M) at pH=3.6, 5.0 and 8.0. In FIGS. 3(a–c) the swelling capacity, Q, can be observed to increase with a decrease in pH. It follows from FIGS. 3a, b and c that the swelling capacity is similar to the hydrogels derived from chitosans with a degree of acetylation of 10 and 28% which swell with very similar profiles, as shown in our previous work [60]. The swelling characteristics and the water content of the hydrogel are listed in Table 6.

TABLE 6

Composition of the swollen hydrogels (spheres)

| DA[a] of Chitosan (%) | Ratio[b] CH/X (g/g) | Composition of Hydrogal | | pH | $\alpha_{max}$[c] (%) | $W_d$ (%) |
|---|---|---|---|---|---|---|
| | | Chitosan (%) | Xanthan (%) | | | |
| 10 | 0.540 | 40.1 | 59.9 | 3.6 | 900 | 90.2 |
| 10 | 0.540 | 40.1 | 59.9 | 5.0 | 490 | 80.4 |
| 10 | 0.540 | 40.1 | 59.9 | 8.0 | 250 | 72.3 |
| 28 | 0.555 | 24.9 | 75.1 | 3.6 | 800 | 87.1 |
| 28 | 0.555 | 24.9 | 75.1 | 5.0 | 560 | 85.2 |
| 28 | 0.555 | 24.9 | 75.1 | 8.0 | 260 | 73.9 |
| 34 | 0.592 | 24.3 | 75.7 | 3.6 | 680 | 88.4 |
| 34 | 0.592 | 24.3 | 75.7 | 5.0 | 240 | 70.3 |
| 34 | 0.592 | 24.3 | 75.7 | 8.0 | 176 | 65.2 |

[a]DA = degree of acetylation.
[b]CH/X ratio of chitosan to xanthan
[c]$\alpha_{max}$ maximum hydrogel swelling
[d]W = water content.

Water constitutes, in all cases, the largest weight of the hydrogel. The large swelling capacity of these hydrogels did not lead to disintegration when prepared as microspheres, as in the case for the chitosan-CMC complex [8].

In order to calculate the effective diffusion coefficient of the RBB-xylan in the porous structure of the xanthan-chitosan hydrogels, a series of experiments were performed under conditions similar to those used in the xylanase hydrolysis experiments reported previously by the inventors [60]. The decrease of the RBB-xylan Concentration in the solution was measured by the absorption at 595 nm. If the mass transfer inside a hydrogel particle is considered to be a pure diffusional phenomenon, and the particles are assumed to be perfect spheres with homogeneous physical properties, the nonsteady state process can be described by the equation 6:

$$\frac{\partial S}{\partial t} = D \left[ \frac{1}{r^2} \cdot \frac{d}{dr} \left( r^2 \cdot \frac{\partial S}{\partial r} \right) \right]$$

where

S=concentration of substrate (RBB-xylan), $M/m^3$ at position r inside the particle S=S(r)

t=time, sec

D=diffusion coefficient r=any radius, (comprised between 0 and $r_p$ (limit value of radius)) with the following initial and boundary conditions:

1. There is no substrate inside the hydrogel particles at the beginning of the experience.
   t=0 S(r)=0 (0<l<$r_p$ at any time S($r_p$)=SE)

2. Due to the spherical symmetry and the homogeneous physical properties, no net transport of substrate occurs from the center of the particle. Thus, at any time:

$$r = 0 \quad \frac{\partial S}{\partial r} = 0 \quad (t \geq 0)$$

3. The diffusional limitations to mass transfer outside the particle can be neglected. Thus, the substrate concentration at the particle-liquid interface is equal to the substrate concentration in the bulk of the liquid phase:

$$s(r_p) = SEP(t) \quad t=0$$

where SEP is the experimentally determined concentration of RBB-xylan in the bulk solution.

Equation (6) combined with a mass balance over the reaction results in the description of the time variation of the substrate concentration in the aqueous phase for a given value of the effective diffusion coefficient. The optimal value of the effective diffusion coefficient can be obtained from the minimization of the following least squares function:

$$\sum_{j=1}^{N} [SEP(t_j) - SE(t_j)]^2 = 0$$

SE is the RBB-xylan concentration in the bulk solution calculated using Equation (6) and the reaction mass balance for a specified value of the effective diffusion coefficient. By using this minimization procedure, an effective diffusion coefficient of $2.02 \times 10^{-12}$ m$^2$/s was found for RBB-xylan in the xanthan-chitosan hydrogel.

The scanning electron microscope (SEM) images of the hydrogels have been obtained for typical gel samples (24.25% chitosan, 75.75% xanthan; data not shown). The images convey the message that the gels are porous and that the formation of fibrillar structures occurred. The channels present in the fibrillar gels have a pore size between $10^{-7}$ and $10^{-6}$ m (0.11 μm). whereas the fibrils have a typical dimension of $10^{-7}$ m (100 nm). The surface of the microsphere has a homogenous porous structure which allows for the passage of polymeric substrates to the regions where the immobilized enzymes are lodged.

By transmission electron microscope (TEM), images of the hydrogels were obtained (data not shown). The presence of loose aggregates of fibrils was observed, probably resulting from the rupture of the elaborate network, observed via SEM, due to the drying and cutting procedures used. The aggregates were formed by fiber fragments with typical diameters of 50 to 100 nm which is in agreement with the SEM observations. Material structure near the external surface of the sample was also evident. The "open spaces" (pores) were well developed towards the center of the sample.

For the chitosan-xanthan complex, the percent of immobilization is a function of the concentration of enzyme in the xanthan solution. The yields of 85–98% of the enzyme are present which is far superior to the immobilization yields obtained by other methods [41–44]. The enzymatic activity of the immobilized xylanase (EC 3.2.1.8) increased with respect to the activity of the free enzyme over a wide range of xylanase concentrations in the xanthan solution (0.21 to 1%) as shown in Table 7.

TABLE 7

Properties of the immobilized enzymes in the chitosan-xanthan hydrogels

| Enzymes | Concentration of Enzymes in the Xanthan Solution (wt %) | Measured Activity[a] (mU/g) | Relative Activity[b] (%) | Limit of Thermal Activity (°C.) |
|---|---|---|---|---|
| Xylanase | 0.21 | 8,889 | +69 | 95[c] |
|  | 0.29 | 11,737 | +61 | 95 |
|  | 0.36 | 16,000 | +77 | 95 |
|  | 1.00 | 26,000 | +2 | 98 |
|  | 1.20 | 28,000 | −7 | 98 |
| Protease | 0.29 | 52,595 | 0 | 77[d] |
|  | 0.69 | 67,900 | 0 | 77 |
|  | 0.96 | 72,187 | −2 | 77 |
|  | 1.88 | 104,294 | −8 | 77 |

[a] Enzyme activity refers to the unit weight of dry hydrogel
[b] Calculated with respect to the initial activity of the xylanase (2,500,000 mU/g) and protease (0.4 U/mg)
[c] Thermal stability of free xylanase = 45° C.
[d] Thermal stability of free protease − 42° C.

Such an increase in activity may be related to a favourable structural effect by the hydrogel on the enzyme through induced electrostatic interactions [45–46]. Such interactions may also explain the observed increase in the thermal stability of the immobilized xylanases which maintained activity up to 98° C.

Figure 4:
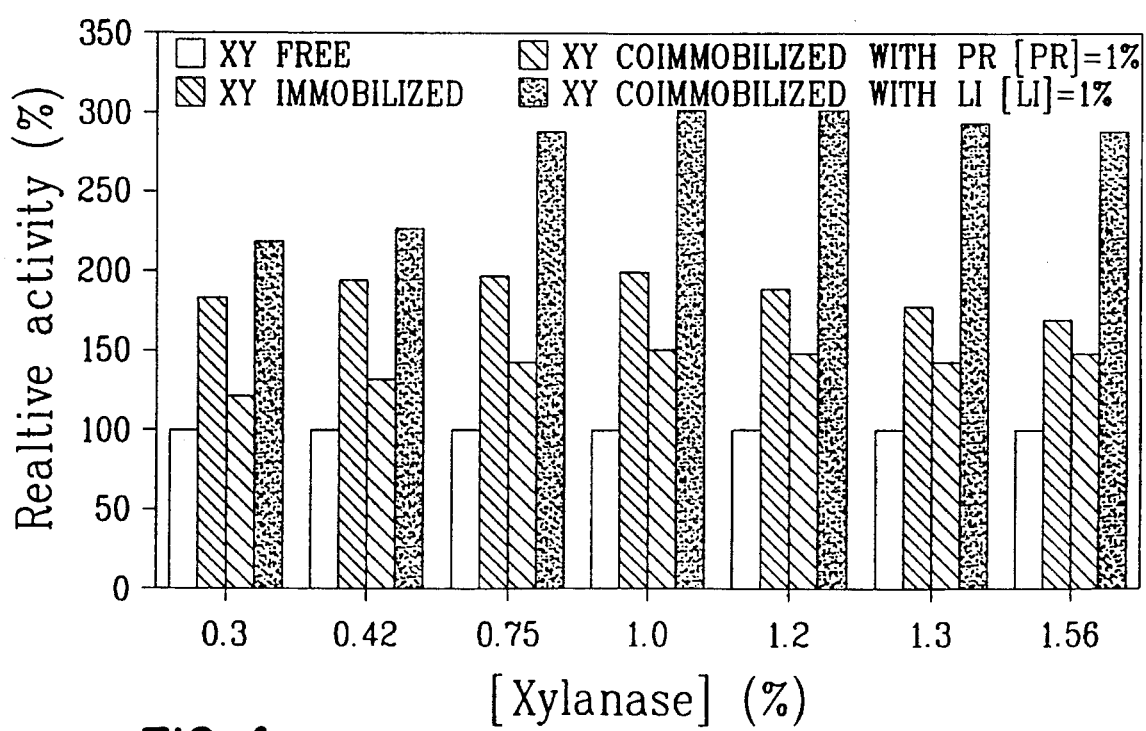
FIG. 4 shows the relative xylanase activity when immobilized in hydrogels alone or co-immobilized in the same with protease (PR), or lipase (LI) as a function of the concentration of xylanase in the solution of xanthan introduced into the solution of chitosan.

In the case of the combined xylanase-protease immobilization as well as for xylanase-lipase, a synergistic effect by the xylanase on the protease and lipase activity was observed (FIG. 4). Such an effect was also observed in the case of immobilized peroxidase-protease combinations [47]. Due to this synergy, the protease activity was increased by 85–200% with respect to that of the free enzyme. The effect seems to be a function of the incubation time. A decrease in the protease activity with the incubation time of the xylanases could be explained by the saturation of the hydrogel with the products of the hydrolysis of the RBB-xylan [48] which would interfere with the diffusion of the hemoglobin needed for hydrolysis by the protease. The optimum incubation conditions appear to be 10 minutes for the xylanases and 50 minutes for the proteases.

CONCLUSIONS

Hydrogels from chitosan and xanthan mixtures can be readily obtained by simple complexation in aqueous phase within wide pH ranges (3.6 to 8.0), the pH having a great influence on the yield of complexation. These gels are insoluble in water and in numerous organic solvents. The yields of complexed chitosan are as high as 98%. The CH/X ratio in the hydrogels and water retention capacity are functions of the degree of acetylation of chitosan and the CH/X ratio used in the initial solution. Hydrogels comprising chitosan are stable in acidic media. Those not containing chitosan (polybasic drugs and xanthan) will slowly dissociated in acidic media, releasing the drugs from the complex. For those particular hydrogels, sustained release compositions are obtained at pH of6 to about 8. Therefore all the hydrogels made in accordance with the present invention are compatible with all the pHs encountered in physiological conditions. These gels will therefore find utility for internal as well as for external use (skin patches, per os compositions, etc.). The hydrogels swell readily with water content between 65 and 95 wt % to of the total mass which is dependent on the cationic component/Xanthan ratio present in the gels.

Structural analysis of the gels made of chitosan/xanthan indicate an open fibrillar structure with characteristic pore dimensions between $10^{-7}$ to $10^{-6}$ m. The fibrils have diameters between 50 and 100 nm.

Due to the immobilization, both the thermal stability and the enzyme activity of the xylanase increased. The protease maintained activity but had lower thermal stability. In the case of the combined immobilization of xylanase and protease, a favourable synergistic effect of the xylanase on the protease activity was observed.

The gels made of chitosan/xanthan can incorporate up to 25% their weight of enzymes and drugs. The composition of the gels may be modified to optimally accommodate the structure and the charges found on single or organized molecules. The xanthan polyanion has been found particularly suitable as a constant component of hydrogels. Therefore, by varying the ratio and the nature of the polycationic components, numerous compositions having the benefit of the present invention are possible.

This invention has been described hereinabove. Modifications thereto will be readily appreciated by the persons skilled in the art without departing from the spirit and the teachings of the present disclosure. These modifications are therefore included in the scope of this invention.

REFERENCES

1. Barnett, S. E. and S. J. Varley. 1987. *Ann. Roy. Coll. Surg Eng.,* 69:153.
2. Burgos, H. 1986. *Eur. J. Clin. Invest.,* 16: 486.
3. Dumitriu, S., N. Aelenei, I. M. Popa, M. Dumitriu and D. Dumitriu. 1992. *Il Farmaco,* 47:509.
4. Dumitriu, S., M. Dumitriu and G. Teaca. 1990. *Clinical Materials,* 6:265.
5. Peppas, N. A. and A. G. Mikos. 1986. *Hydrogels in Medicine and Pharmacy,* Vol. 1, *Fundamentals,* N. A. Peppas, ed., Boca Raton, Fla.: CRC Press, Inc, pp 2–24.
6. Yoshioka, T., R. Hirano. T. Shioya and M. Kako 1990. *Biotechnol. Bioeng,* 35:66.
7. Crescenzi, V., M. Demtini and R. Rizzo. 1981. *ACS Symposium Series,* 150:331.
8. Shioya, T. and C. K. Rha. 1989. *Chitin and Chitosan,* G. Skjak-Braek, T. Anthonsen, and P. Sandford, eds., London and New York: Elsevier Appl. Sci., p. 627.
9. Lemainque, A., J. Braun and F. Le Goffic 1988. *Eur. J. Biochem.,* 174:171.
10. and D. Knorr. =1990. *International Conference on Biotechnology and Food,* Stuttgart, Germany, Feb. 20–24, 1989, Food Biotechnol. N.Y. (1) p. 484.
11. Shaw, J. F., R. C. Chang, F. F. Wang and Y. J. Wang. 1990. *Biotechnol. Bioeng,* 35:132.
12. Hisamatsu, M. and T. Yamada. 1989. *J. Ferment. Bioeng,* 67:219.
13. Peleg, K. and C. Rha. 1989. *J. Rheol.,* 32:367.
14. Kibuchi, Y. and N. Kubota, 1985. *J. Polym. Sci., Polym. Lett.* Ed., 23:537.
15. Kise, H., A. Hayakawa and H. Noritomi. 1987. *Biotechnol. Lett.,* 9:543.
16. Zielinski, B. A. and P. Aebischer. 1994. *Biomaterials,* -15: 1049.
17. Mitsutomi, M., Y. Uchida and A. Ohtakara. 1985. *J. Ferment. Technol.,* 63:325.
18. Hirano, S. and K. Horiuchi. 1989. Int. *J. Biol Macromol.,* 11:254.
19. Aiba, S. 1989. Int. *J. Biol Macromol.,* 11:249.
20. Bogdansky, S. 1990. *Biodegradable Polymers as Drug Delivery Systems,* M. Chasin and R. Langer, eds. Marcel Dekker, New York, p. 231.
21. Struszczyk, H. 1987. *J. Appl Polym. Sci.,* 33:177.
22. Kifune, K. 1992. *Advances in Chitin and Chitosan,* C. J. Brine, P. A. Sandford and J. P. Zikakis, eds., Elsevier Appl. Sci., p. 9.
23. Domszy, J. G., G. A. F. Roberts and F. A. Wood. 1986. *Chitin in Nature and Technology,* R. Muzzarelli, C. Jeuniaux and G. W. Gooday, eds., London and New York: Plenum Press, p. 311.
24. Brine, C. J. 1988. *Chitin and Chitosan,* G. Skjak-Braek, T. Anthonsen and P. Sandford eds., London and New York: Elsevier Appl. Sci., p. 679.
25. Battilotti, M. and U. Barberini. 1988. *J. Moles. Catal,* 43:343.
26. Kennedy, J. F. and M. Paterson. 1993. *Polym Int.,* 32:71.
27. Chibata, I., T. Tosa and T. Sato. 1986. *J. Mol Catal.,* 37:1.
28. Simionescu, C., S. Dumitriu, V. Artenie and M. Popa 1986. *Reactive Polymers,* 4:237.
29. Phadke, R. S. 1992. BioSystems, 27:203.
30. Goosen, M. F. A., G. M. O'Shea, H. F. Gharapetian, S. Chou and A.M. Sun. 1985. Biotechn. Bioeng., 27:146.
31. Nilson, K., W. Scheirer, O. W. Merten, L. Ostberg, E. Liehl, H. W. D. Katinger and K. Mosbach. 1983. Nature, 302:629.
32. Scheirer, W., K. Nilsson, O. W. Merten, H. W. D. Katinger and K. Mosbach. 1984. Develop. Biol. Standard., 55:155.
33. Guit, R. P. M., M. Kloosterman, G. W. Meindersma, M. Mayer and E. M. Meijer. 1991. *Biotechn. Bioeng.,* 38:727.
34. Jamuna, R. and S. V. Ramakrishna. 1992. *Enzyme Microb. Technol.,* 14:36.
35. Roberts, G. A. F. and J. G. Domszy. 1982. *Int. J. Biol. Macromol.,* 4:374.
36. Kim, K. S. and C. K. Rha. 1989. *Chitin and Chitosan,* G. Skjak-Braek, T. Anthonsen and P. Sandford, eds., London and New York: Elsevier Appl. Sci., p. 617.
37. Melia, C. D. 1991. *Critical Rev. Therap. Drug Carrier Systems,* 8:395.
38. Beldie, C., S. Dumitriu, N. Aelenei, M. Popa, M. I. Popa and D. Dumitriu. 1989. *Biopolymers,* 10:622.
39. Biely, P., D. Mislovicova and R. Toman. 1988. *Methods in Enzymology,* Vol. 160, W. A. Wood and S T. Kellogg, eds., New York: Academic Press Inc, p. 536.
40. Sarah, G., R. S De la Motte and F. W. Wagner. 1989. *Proteolytic Enzymes a Practical Approach,* R. J. Beynon and J. S. Bond, eds., Oxford, New York, Tokyo: IRL Press, p. 25.
41. Shaw, J. F., R. C. Chang, F. F. Wang and Y. J. Wang 1990. *Biotechnol. Bioeng,* 35:132.
42. Uo, M., M. Numata, M. Suzuki, E. Tamiya, I. Karube and A. Makishima. 1992. J. Ceramic Soc. Jpn., 100:430.
43. Wallbanks, K. R., D. H. Molyneux and M. F. Dirie. 1989. *Acta Trop* (Basel), 46:63.
44. Kise, H. and A. Hayakawa. 1991. Enzyme Microb. Technol., 14:36.
45. Simpson, H. D., U. R. Haufler and R. M. Daniel. 1991. *Biochem. J.,* 277(Pt. 2):413.
46. Gianfreda, L. and M. R. Scarfi. 1991. *Molec Cell. Biochem.,* 100:97.
47. Grzywnowicz, K., H. Greppin, M. Brzyska and J. Lobarzewski. 1993. *J. Molec Cat.,* 80:117.
48. Puls, J., A. Borchmann, D. Gottschalk and J. Wiegel. 1988. *Methods in Enzymology,* Vol. 160, W. A. Wood and S T. Kellogg, ads., New York: Academic Press, Inc., p. 528.
49. Mansfeld, J. M. Förster, A. Schellenberger and H. Dautzenber. 1991. *Enzyme Microb. Technol.* 13:240.

50. Kikuchi, Y. and N. Kubota. 1985. *Makromol. Chem., Rapid Commun.*, 6:387.
51. Chavasit, V. and J. A. Torres. 1990. *Biotechnol. Prog.*, 6:2.
52. Fukuda, H. and Y. Kikuchi. 1978. *Bull. Chem. Soc. Jpn.*, 51:1142.
53. Kikuchi, Y. and A. Noda. 1976. *J. Appl. Polym. Sci.*, 20:2561.
54. Kikuchi, Y. and H. Fukuda. 1974. Polyelectrolyte complexes of sodium dextran sulfate with chitosan, *Makromol. Chem.*, 175:3593.
55. Daly, M. M. and D. Knorr. 1988. *Progress Biochem.*, 48:48.
56. Mireles, C. M. Martino, J. Bouzas and J. A. Torres. 1992. *Advances in Chitin and Chitosan* C. J. Brine, P. A. Sandford, J. P. Zikakis, Ed, Elsevier Appl. Sci., p. 506.
57. Hirano, S. C. Mizutani, R. Yamaguchi, and O. Miura. 1978. *Biopolymers*, 17:805.
58. Fukuda, H. 1980. *Bull. Chem. Soc. Jpn.*, 53:837.
59. Rathke, T. D. and S. M. Hudson. 1994. *J. M. S. -Rev. Macromol. Chem. Phys.*, C34: 375.
60. Dumitriu, S., P. Magny, D. Montane, P. F. Vidal, and E. Chornet. 1994. by complexation between xanthan and chitosan: Their properties as supports for enzyme immobilization, *J. Bioactive Compat. Polym.*, 9: 184.

What is claimed is:

1. A water insoluble porous hydrogel for use in encapsulation and controlled release of a biologically active substance, which comprises:

chitosan;

xanthan; and said biologically active substance;

the chitosan and xanthan being present in said hydrogel in proportions ranging from about 24–40% of chitosan and about 60–76% of xanthan.

2. A hydrogel as defined in claim 1, wherein said biological substance is selected from the group consisting of prokaryotic cells, eucaryotic cells, proteins and drugs.

3. A hydrogel as defined in claim 2, wherein said drugs are selected from the group consisting of cephalosporin, tetracyline, oxytetracycline, sulfathiazole, metronidazole, chloramphenicol, daunorubicin, ampicillin, penicillin, erthromycin, quinidine, alacacinomycin, mithramycin, gentamycin, bleomycin, anthelmycin, enzomycin A, vancomycin, trichomycin, adenomycin, orthomycin, neomycin, kanamycin and sisomycin.

4. A hydrogel as defined in claim 2, wherein said proteins are enzymes selected from the group consisting of xylanase, lipase, hemicellulase, protease and mixtures of xylanase/lipase, xylanase/protease and xylanase/hemicellulase.

* * * * *